United States Patent

Hosokawa et al.

Patent Number: 5,369,085
Date of Patent: Nov. 29, 1994

[54] INDANE-1, 3-DIONE DERIVATIVES AND HERBICIDES CONTAINING THEM AS ACTIVE INGREDIENT

[75] Inventors: Akemi Hosokawa, Yokohama; Osamu Ikeda, Machida; Noriko Minami, Setagaya; Nobuo Kyomura, Sagamihara, all of Japan

[73] Assignee: Mitsubishi Kasei Corporation, Tokyo, Japan

[21] Appl. No.: 28,185

[22] Filed: Mar. 9, 1993

[30] Foreign Application Priority Data

Mar. 10, 1992 [JP] Japan .................................. 4-051590

[51] Int. Cl.$^5$ .................... A01N 43/02; C07D 303/32
[52] U.S. Cl. .................... 504/249; 504/348; 568/327; 546/340
[58] Field of Search ................ 568/327; 504/348, 249; 546/340

[56] References Cited

FOREIGN PATENT DOCUMENTS 0398258 11/1990 European Pat. Off. .

Primary Examiner—Johann Richter
Assistant Examiner—Catherine Scalzo
Attorney, Agent, or Firm—Wenderoth, Lind & Ponack

[57] ABSTRACT

Indane-1, 3-dione derivatives of the following general formula [I]:

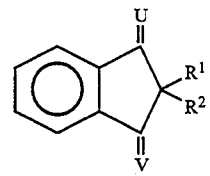

and herbicidal compositions containing them as an active ingredient are provided. The derivatives are highly valuable in exhibiting excellent herbicidal activity while causing markedly low damage on crops.

11 Claims, No Drawings

INDANE-1, 3-DIONE DERIVATIVES AND HERBICIDES CONTAINING THEM AS ACTIVE INGREDIENT

The present invention relates to novel indane-1, 3-dione derivatives and herbicidal composition containing them as an active ingredient.

Numerous compounds having indane-1, 3-dione structure have been known, and those which show a particular physiological activity share a common fundamental structure. An illustrative example of the fundamental structure is 2-(aryl or aryl substituted acyl) indane-1, 3-dione, which is known to be useful as a rat poison.

Further examples are 1, 3-dimethyl-(substituted benzoyl)-5-(indane-1, 3-dione-2-yloxy)pyrazole having a herbicidal activity (Japanese Patent Publication (Kokai) No. 118003/1981), and 2-substituted-2-alkyl-indane-1, 3-dione derivatives having a herbicidal activity (Japanese Patent Publication (Kokai) No. 304043/1990).

Many herbicidal compounds have heretofore been proposed, but there are not so many herbicides exhibiting both negligible damage on desired crops and satisfactory herbicidal activity on undesirable weeds. On the other hand, as small a dosage as possible of herbicides is desired from the viewpoint of environmental pollution. Thus, it has been a continuous desire to develop a herbicidal compound which will meet the requirements just mentioned above.

As the result of extensive studies for coping with such requirements, the present inventors have succeeded in finding novel indane-1, 3-dione derivatives having excellent herbicidal activities.

Thus, the present invention is directed to indane-1, 3-dione derivatives of the following general formula [I]:

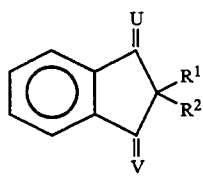

wherein $R^1$ represents $C_2-C_{10}$ alkenyl group, $C_2-C_6$ alkynyl group, $C_1-C_6$ haloalkyl group, $C_2-C_6$ haloalkenyl group, $C_2-C_6$ haloalkynyl group, $C_1-C_4$ hydroxyalkyl group, $C_2-C_8$ alkoxyalkyl group, $C_2-C_5$ alkoxycarbonyl group, $C_1-C_6$ alkylthio group, optionally substituted phenylthio group, $C_1-C_6$ alkylsulfinyl group, optionally substituted phenylsulfinyl group, $C_1-C_6$ alkylsulfonyl group, optionally substituted phenylsulfonyl group, $C_1-C_4$ haloalkylsulfonyl group, cyano group, halogen atom, $C_2-C_5$ alkylcarbamoyl group, $C_2-C_5$ cyanoalkyl group, $C_2-C_5$ acyloxyalkyl group, $C_3-C_6$ epoxyalkyl group, $C_2-C_5$ acyl group or $-CH_2-A$, in which A represents optionally substituted phenyl group, pyridyl group, thiazolyl group or oxiranyl group, $R^2$ represents

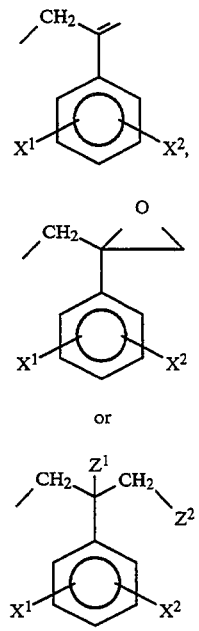

in which $X^1$ and $X^2$ each independently represent hydrogen atom, halogen atom, $C_1-C_4$ alkyl group, $C_1-C_3$ haloalkyl group or nitro group, $Z^1$ and $Z^2$ each independently represent hydroxy group, halogen atom, optionally substituted $C_1-C_4$ alkylsulfonyloxy group or optionally substituted phenylsulfonyloxy group, U and V each independently represent oxygen atom, sulfur atom or $NHOR^3$, in which $R^3$ represents hydrogen atom, $C_1-C_4$ alkyl group or $C_2-C_4$ acyl group.

The present invention is also directed to a herbicidal composition containing at least one of the compounds of the present invention as an active ingredient together with a carrier therefor. The present invention will be explained below in more detail.

The indane-1, 3-dione derivatives used in the present invention are represented by the general formula [I] above, and preferable substituents in the general formula [I] will be illustrated below. However, the scope of the present invention should not be limited to the following illustrations.

$R^1$ represents $C_2-C_{10}$, preferably $C_2-C_6$, straight or branched alkenyl group such as vinyl group, allyl group, 1-propenyl group, 1-methylvinyl group, 2-butenyl group, 3-butenyl group, 1-methylallyl group, 2-methylallyl group, 2-pentenyl group, 3-pentenyl group, 4-pentenyl group, 1-methyl-2-butenyl group, 3-methyl-2-butenyl group, 2-methyl-3-butenyl group, 3-methyl-3-butenyl group, 1-methyl-3-butenyl group, geranyl group or the like; $C_2-C_6$, preferably $C_2-C_4$, straight or branched alkynyl group such as ethynyl group, propargyl group, 1-methyl-2-propynyl group, 1, 1-dimethyl-2-propynyl group or the like; $C_1-C_6$ haloalkyl group, preferably $C_1-C_3$ haloalkyl group containing one to three fluorine or bromine atoms, such as fluoromethyl group, chloromethyl group, bromomethyl group, difluoromethyl group, trifluoromethyl group, chlorodifluoromethyl group, bromodifluoromethyl group, 2-fluoroethyl group, 2-chloroethyl group, 2-bromoethyl group, 1-chloro-2, 2, 2-trichloroethyl group, 2, 2, 2-trifluoroethyl group or the like; $C_2-C_6$ haloalkenyl group, preferably $C_2-C_4$ haloalkyl group containing one to three chlorine atoms, such as 2, 3-dichloroethenyl group, 2, 3-bromoethenyl group, 2, 3-difluoroethenyl group, 2-chloro-2-propenyl group, 2-bromo-2-propenyl group, 2-fluoro-2-propenyl group, 3-chloro-2-propenyl group, 3, 3-dichloro-2-propenyl group, or the like; $C_2$–$C_6$ haloalkynyl group such as 3-iodo-2-propynyl group or the like; $C_1$–$C_4$ hydroxyalkyl group such as hydroxymethyl group, 2-hydroxyethyl group, 3-hydroxypropyl group, 4-hydroxybutyl group, or the like; $C_2$–$C_8$ alkoxyalkyl group such as methoxymethyl group, 2-methoxyethyl group, 3-methoxypropyl group, 4-methoxybutyl group, 2-ethoxyethyl group, 2-butoxyethyl group or the like; $C_2$–$C_5$, preferably $C_2$–$C_4$, alkoxycarbonyl group such as methoxycarbonyl group, ethoxycarbonyl group, propoxycarbonyl group, isopropoxycarbonyl group, butoxycarbonyl group, or the like; $C_1$–$C_6$ alkylthio group such as methylthio group, ethylthio group, propylthio group, isopropylthio group, butylthio group or the like; optionally substituted phenylthio group such as phenylthio group, o-chlorophenylthio group, m-chlorophenylthio group, p-chlorophenylthio group, o-methylphenylthio group, m-methylphenylthio group, p-methylphenylthio group or the like; $C_1$–$C_6$ alkylsulfinyl group such as methylsulfinyl group, trifluoromethylsulfinyl group, ethylsulfinyl group, propylsulfinyl group, isopropylsulfinyl group, butylsulfinyl group or the like; optionally substituted phenylsulfinyl group such as phenylsulfinyl group, o-chlorophenylsulfinyl group, m-chlorophenylsulfinyl group, p-chlorophenylsulfinyl group, o-methylphenylsulfinyl group, m-methylphenylsulfinyl group, p-methylphenylsulfinyl group or the like; $C_1$–$C_6$ alkylsulfonyl group such as methylsulfonyl group, trifluoromethylsulfonyl group, ethylsulfonyl group, propylsulfonyl group, isopropylsulfonyl group, butylsulfonyl group, or the like; optionally substituted phenylsulfonyl group such as phenylsulfonyl group, o-chlorophenylsulfonyl group, m-chlorophenylsulfonyl group, p-chlorophenylsulfonyl group, o-methylphenylsulfonyl group, m-methylphenylsulfonyl group, p-methylphenylsulfonyl group or the like; $C_1$–$C_4$ haloalkylsulfonyl group such as trifluoromethylsulfonyl group, trichloromethylsulfonyl group or the like; cyano group; such as fluorine atom, chlorine atom, bromine atom or the like; $C_2$–$C_5$ alkylcarbamoyl group such as N-methylcarbamoyl group N-ethylcarbamoyl group, N-propylcarbamoyl group or the like; $C_2$–$C_5$ (including the carbon atom of cyano group) cyanoalkyl group such as cyanomethyl group, 1-cyanoethyl group, 2-cyanoethyl group, 3-cyanopropyl group or the like; $C_2$–$C_5$ acyloxyalkyl group such as acetoxymethyl group, propionyloxymethyl group or the like; $C_2$–$C_5$ acyl group such as acetyl group, propionyl group, butyryl group, isobutyryl group or the like; —$CH_2$–A, in which A represents optionally substituted phenyl group; optionally substituted pyridyl group; optionally substituted thiazolyl group; oxiranyl group such as 2, 3epoxyethyl, 2, 3-epoxy-2-methylethyl group or the like. Examples of the substituent on the phenyl group, pyridyl group and thiazolyl group are halogen atom such as fluorine atom, chlorine atom, bromine atom or the like; $C_1$–$C_3$ alkyl group such as methyl group, ethyl group, propyl group or the like; hydroxy group; $C_1$–$C_4$ alkoxy group such as methoxy group, ethoxy group, n-propoxy group, isopropoxy group, n-butoxy group, isobutoxy group, sec-butoxy group, t-butoxy group or the like; $C_1$–$C_4$ alkylthio group such as methylthio group, ethylthio group, n-propylthio group, isopropylthio group, n-butylthio group or the like; nitro group; cyano group or the like. Preferably, A represents halogen atom, phenyl or pyridyl group, optionally substituted with halogen atom or alkoxy group.

$R^2$ represents

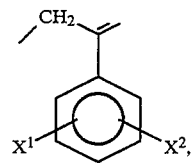

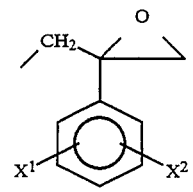

or

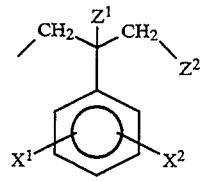

wherein $X^1$ and $X^2$ each independently represent hydrogen atom; halogen atom such as fluorine atom, chlorine atom, bromine atom, iodine atom or the like; $C_1$–$C_4$ alkyl group such as methyl group, ethyl group, n-propyl group, isopropyl group, n-butyl group, isobutyl group or the like; $C_1$–$C_3$ haloalkyl group such as difluoromethyl group, trifluoromethyl group, trichloromethyl group or the like; or nitro group, and preferably one of $X^1$ and $X^2$ is chlorine atom and the other is hydrogen atom, and more preferably one of $X^1$ and $X^2$ is chlorine atom at m-position and the other is hydrogen atom; $Z^1$ and $Z^2$ each independently represent hydroxy group; halogen atom such as chlorine atom, bromine atom or the like; optionally substituted $C_1$–$C_4$ alkylsulfonyloxy group such as methylsulfonyloxy group, trifluoromethylsulfonyloxy group, ethylsulfonyloxy group or the like; optionally substituted phenylsulfonyloxy group such as phenylsulfonyloxy group, o-chlorophenylsulfonyloxy group, m-chlorophenylsulfonyloxy group, p-chlorophenyl sulfonyloxy group, o-methylphenylsulfonyloxy group, m-methylphenylsulfonyloxy group, p-methylphenylsulfonyloxy group or the like, and preferably $Z^1$ is hydroxy group and $Z^2$ is hydroxy group or alkylsulfonyl group; and U and V represent oxygen atom, sulfur atom or $NHOR^3$, in which $R^3$ represents hydrogen atom, $C_1$–$C_4$ alkyl group such as methyl group, ethyl group, n-propyl group, isopropyl group, n-butyl group, isobutyl group or the like; or $C_2$–$C_4$ acyl group such as acetyl group, propionyl group, butyryl group, isobutyryl group or the like, and preferably U and V are both oxygen atoms.

The process for the production of the compounds of the present invention will be explained below.

The compounds of the present invention of the general formula [I] can be prepared, for example, according to one of the following schemes (1), (2), (3), (4), (5), (6), (7), (8), (9) and (10):

(1)

[Structural reaction scheme showing compound [II] + [III] → [Ia]]

In the above formulae, $W^1$ represents halogen atom, alkylsulfonyloxy group or optionally substituted phenylsulfonyloxy group, U, V, $R^1$, $X^1$ and $X^2$ have the same meanings as defined in the general formula [I] above.

The reaction can be effected in the presence or absence of a base in a solvent or without solvent. When a solvent is used, suitable solvents are aromatic hydrocarbons such as benzene, toluene, xylene or the like; ethers such as diethyl ether, tetrahydrofuran, dioxane, ethylene glycol dimethyl ether or the like; esters such as methyl acetate, ethyl acetate or the like; ketones such as acetone, methyl ethyl ketone or the like; polar solvents such as water, N, N-dimethylformamide, N-methylpyrrolidone, dimethylsulfoxide, acetonitrile or the like.

Examples of the base used in the reaction are triethylamine, pyridine, picoline, N, N-dimethylaniline, sodium hydrogencarbonate, potassium hydrogencarbonate, sodium carbonate, potassium carbonate, sodium hydroxide, potassium hydroxide, sodium ethylate, sodium methylate, sodium hydride, lithium N, N-diisopropylamine, 1, 8-diazabicyclo-[5, 4, 0]-7-undecene and the like.

The reaction is effected usually at temperature from −20° to 200° C., preferably −5° to 120° C., for a period of 0.5 to 48 hours, usually 1 to 12 hours.

The starting compound (II) can be prepared, for example, according to the method described by Moses, Pinchas; Dahlbom, Richard, Acta. Pharm. Suecica 1969 6 (3), pp.359-72.

(2)

[Structural reaction scheme showing compound [IV] + $R^1W^2$ → [Ia]]

In the above formulae, $W^2$ represents chlorine atom, bromine atom, iodine atom or alkylsulfonyloxy group, and U, V, V $R^1$, $X^1$ and $X^2$ have the same meanings as defined in the general formula (I) above.

The reaction is effected in the presence or absence of a base with or without a solvent. Suitable solvents and bases are the same as those described in the foregoing scheme (1). The reaction is effected usually at temperature from −20° to 200° C., preferably −5° to 120° C., for a period of 0.5 to 48 hours, usually 1 to 12 hours.

The starting compound [IV] is prepared by reacting 1, 3-indanedione with the compound [III] above.

(3)

[Structural reaction scheme showing compound [Ib] + Sulfur-containing reagent → [Ic]]

In the above formulae, at least one of $U^1$ and $V^1$ represents sulfur atom, and the other represents oxygen atom or sulfur atom, and $R^1$, $X^1$ and $X^2$ have the same meanings as defined in the general formula (I) above.

The reaction can be effected in the presence of a sulfur-containing reagent with or without solvent. The sulfur-containing reagent includes phosphorus pentasulfide, Lawson reagent and the like. Suitable solvents are those described in Scheme (1).

The reaction is effected usually at temperature from −20° to 200° C., preferably 0° to 200° C., for a period of 1 to 48 hours.

(4)

[Structure Ib] + NH$_2$OR$^3$ →

[Structure Id]

In the above formulae, at least one of U$^1$ and V$^1$ represents NHOR$^3$, and the other represents oxygen atom or NHOR$^3$, and R$^1$, R$^3$, X$^1$ and X$^2$ have the same meanings as defined in the general formula (I) above.

The reaction can be effected in the presence or absence of a base with or without solvent. Suitable solvents and bases are those described in Scheme (1).

The reaction is effected usually at temperature from −20° to 200° C., preferably −5° to 120° C., for a period of 0.5 to 48 hours, usually 1 to 12 hours.

(5)

[Structure Ia] —Oxidation→ [Structure Ie]

In the above formulae, U, V, R$^1$, X$^1$ and X$^2$ have the same meanings as defined in the general formula (I) above.

The oxidation is effected in the presence of an oxidant such as peroxides, such as m-chloroperbenzoic acid, peracetic acid or the like, hydrogen peroxide, t-butyl hydroperoxide, alkali metal hypohalite or the like, in a solvent such as chloroform, methylene chloride, carbon tetrachloride, benzene, cyclohexane, n-hexane, methanol, ethanol, propanol, butanol, acetic acid, water or the like. The reaction is usually effected at temperature from −20° to 120° C., preferably 0° to 80° C., usually for a period of 1 to 24 hours, preferably 1 to 12 hours.

(6)

[Structure Ia] —Halogen-containing reagent→

[Structure II]

In the above formulae, Z$^2$ represents halogen atom, and U, V, R$^1$, X$^1$ and X$^2$ have the same meanings as defined in the general formula (I) above.

The reaction is effected by reacting Compound [Ia] with a halogen-containing reagent such as alkali metal hypohalite, alkali metal halite, N-halogenosuccinimide, chlorine, bromine, iodine or the like, in the presence or absence of a fatty acid (e.g. acetic acid ), mineral acid and/or heavy metal compound such as mercury acetate, mercuric oxide or the like, in water or an aqueous solvent. This reaction is carried out usually at temperature from − 30° to 100° C. preferably −10° to 60° C., usually for a period of 0.1 to 24 hours, preferably 0.5 to 6 hours.

(7)

[Structure Ia] →

-continued

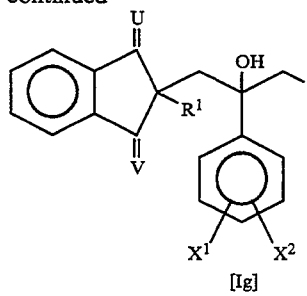

[Ig]

In the above formulae U, V, $R^1$, $X^1$ and $X^2$ have the same meanings as defined in the general formula (I) above.

This reaction corresponds, in general, to the oxidation of olefines to 1, 2-diols according to the teaching of organic chemistry. This reaction is extensively described in published literatures, for example, Alan H. Haines, "Methods for the Oxidation of Organic Compounds", pp. 73–93 (1985), Academic Press.

This reaction is effected by reacting Compound (Ia) with hydrogen peroxide and fatty acid (e.g. formic acid, acetic acid) usually at 0° to 120° C., preferably 20° to 80° C., for a period of 0.5 to 24 hours, preferably 1 to 12 hours, and treating the reaction mixture with an aqueous alkaline solution (e.g. sodium hydroxide) usually at 0° to 100° C., preferably 20° to 80° C.

(8)

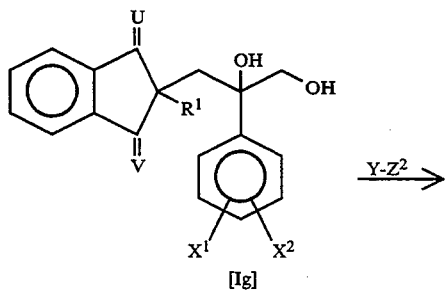

[Ig]

[Ih]

In the above formulae, $Z^2$ represents optionally substituted alkylsulfonyloxy group or optionally substituted phenylsulfonyloxy group, Y represents halogen atom, optionally substituted alkylsulfonyl group or optionally substituted phenylsulfonyl group, and $X^1$, $X^2$, $R^1$, U and V have the same meanings as defined in the general formula (I) above. The group Y-$Z^2$ illustratively means methanesulfonyl chloride, p-toluenesulfonyl chloride and sulfonic acid anhydride.

The sulfonylation can be effected in the presence or absence of a base with or without solvent. When a solvent is used, appropriate solvents illustratively include N, N-dimethylformamide, N-methylpyrrolidone, tetrahydrofuran, dioxane, 1, 2-dimethoxyethane, benzene, toluene, ethyl acetate, methylene chloride, chloroform, and the like. The base includes pyridine, triethylamine, N, N-dimethyl (diethyl) aniline, sodium (potassium) bicarbonate, sodium (potassium) carbonate, sodium (potassium) hydroxide, and the like. The reaction is effected usually at temperature from −20° to 100° C. preferably 0° to 60° C., usually for a period of 1 to 24 hours.

(9)

[Ii]

[Ie]

In the above formulae U, V, $R^1$, $Z^2$, $X^1$ and $X^2$ have the same meanings as defined in the general formula (I) above.

The reaction can be effected in the presence of a base such as sodium (potassium) bicarbonate, sodium (potassium) carbonate, sodium (potassium) hydroxide, sodium hydride, sodium alcoholate, pyridine, triethylamine, N, N-dimethyl (diethyl) aniline or the like, in a solvent selected from methanol, ethanol, 2-propanol, acetone, ethyl methyl ketone, ether, tetrahydrofuran, dioxane, benzene, toluene, ethyl acetate, N, N-dimethylformamide, dimethyl sulfoxide, N-methylpyrrolidone, acetonitrile, water and the like, or a mixture thereof, usually at temperature from −10° to 120° C., preferably 0° to 80° C. Reaction time usually ranges from 0.1 to 12 hours.

(10)

[Ie]

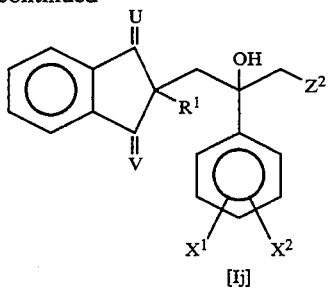

[Ij]

In the above formulae, $Z^2$ represents halogen atom, optionally substituted alkylsulfonyloxy group or optionally substituted phenylsulfonyloxy group, and $R^1$, U, V, $X^1$ and $X^2$ have the same meanings as defined in the general formula (I) above.

The reaction is effected by reacting Compound [Ie] with a hydrogen halide or sulfonic acid in the presence or absence of organic bases (e.g. pyridine, picoline, quinoline, etc.) or inorganic bases (e.g. sodium (potassium) hydroxide, sodium (potassium) carbonate, sodium (potassium) bicarbonate, etc. in a solvent selected from water, diethyl ether, diisopropyl ether, tetrahydrofuran, dioxane, benzene, toluene, methylene chloride, chloroform, carbon tetrachloride, N, N-dimethylformamide, N-methylpyrrolidone, ethyl acetate, 2-propanol, 2-methyl-2-propanol, water and the like, or a mixture thereof. This reaction is carried out usually at temperature of from −120° to 150° C., preferably −60° to 80° C., usually 0.1 to 48 hours, preferably 0.5 to 12 hours.

The compounds of the present invention can exist as an optical isomer although they are usually prepared as a racemate. Each isomer can be prepared by known asymmetric synthesis. The compounds of the present invention can be used as herbicides in the form of racemate or isomers.

The compounds (I) of the present invention alone can be used as herbicides. However, it may be preferable to use them in the form of an appropriate formulation such as wettable powders, granules, emulsions, flowables or the like, which are prepared by mixing them with appropriate carriers or surfactants in a conventional manner. Appropriate carriers and surfactants are described, for example, in Japanese Patent Publication (Kokai) No. 25986/1985. The herbicides containing the compound (I) of the present invention can be applied in combination with other agricultural chemicals used in the same art field, such as insecticides, fungicides, herbicides, plant growth regulators or manures.

The amount of the compound (I) to be applied to the locus where undesired plants should be eradicated or eliminated differs depending upon particular compound (I) to be used, weeds to be destroyed, application time, application method or soil conditions, but it is in general 0.2 to 40 grams, preferably 1 to 20 grams, per are.

The compounds of the present invention exhibit slight variation in their physiological activities depending upon functional groups contained and position of substituents. However, every compound of the invention shows very potent herbicidal activity to barnyard grass (*Echinochloa Crusgalli*), one of the most harmful weeds in the rice plant cultivation in paddy field, without causing detectable injury to rice plant. The compounds are effective to weeds both before and after emergence.

The compounds of the present invention can effectively be applied not only to paddy soil but also to farmland soil. Thus, the compounds show potent herbicidal activity to annual weeds such as large crabgrass (*Digitaria adscendens*), barnyard grass (*Echinochloa Crus-galli*), green foxtail (*Setaria viridis*) or the like, and very little harm to crops such as soybean, cotton, corn, wheat, barley, beet or the like.

The compounds of the present invention show highest herbicidal activity to graminaceous weeds such as large crabgrass, barnyard grass, and green foxtail or the like. However, they also show sufficient activity to cyperaceous weeds such as nutsedge (*Cyperus microiria*), umbrella plant (*Cyperus difformis*), hardstem bulrush (*Scirpus juncides*), slender spikerush (*Eleocharis acicularis*) or the like, and annual weeds such as common lambsquarters (*Chenopodium album*), redroot pigweed (*Amaranthus retroflexus*), smartweed (*Polygonum blumei*), indian toothcup (*Rotala indiea*), pickerelweed (*Monochoria vaginalis*) or the like.

Among typical compounds of the present invention listed in Tables 1-3, Compound Nos. 10, 27, 28, 31, 36, and 40 are especially preferable in the light of their herbicidal activities.

The compounds of the present invention show comparatively weak herbicidal activity to matured annual broad-leaf weeds and perennial weeds. However, the herbicidal spectra can be markedly enlarged by mixing the compounds of the invention with other herbicides effective to the above-mentioned weeds. The compounds of the invention are also useful for stabilizing herbicidal activities of other herbicides.

Appropriate other herbicides mixable with the compounds of the invention are described, for example, in Japanese Patent Publication (Kokai) No. 304043/1990, pp. 22-32. Two or more other herbicides can be mixed with the compound of the invention.

The following detailed examples are presented by way of illustration of certain specific embodiments of the invention. The examples are representative only and should not be construed as limiting the present invention in any respect.

EXAMPLE 1.

Production of 2-benzyl-2-[2-(3-chlorophenyl)-2-propenyl]indane-1, 3-dione

To a solution of 3.0 g of 2-benzylindane-1, 3-dione in 50 ml of dimethylcellosolve were added 5.3 ml of 20% aqueous potassium hydroxide and 2.5 g of 3-chloro-α-(chloromethyl) styrene, and the resultant mixture was stirred at 80° C. for 3 hours. The reaction mixture was mixed with dilute hydrochloric acid and extracted with ethyl acetate. The organic layer was dried over anhydrous magnesium sulfate, and the solvent was evaporated. The residue was chromatographed on a silica gel column, eluting with n-hexane/ethyl acetate (6:1) to give 2.68 g of Compound No. 18 listed in Table 1 below.

EXAMPLE 2.

Production of 2-allyl-2-[2-(3-chlorophenyl)-2-propenyl]indane-1, 3-dione

To a solution of 2.6 g of 2-[2-(3-chlorophenyl)-2-propenyl]indane-1, 3-dione in 20 ml of acetone were added 1.8 g of potassium carbonate and 1.3 g of allyl bromide, and the resultant mixture was stirred at 80° C. for 2 hours. After evaporation of the solvent in vacuo, the residue was mixed with water and extracted with ethyl acetate. The 10 organic layer was dried over anhydrous magnesium sulfate and the solvent was evaporated. The residue was chromatographed on a silica gel column, eluting with n-hexane/ethyl acetate (6:1) to give 2.1 g of Compound No. 9 listed in Table 1 below.

In accordance with the methods as described above, the compounds of Table 1 were prepared. The structures of the compounds were confirmed by measuring IR spectra and $^1$H-NMR spectra. The number in "Synthetic Method" represents the Example number.

TABLE 1

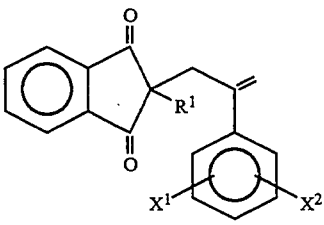

| Compound No. | $R^1$ | $X^1$ ⌬ $X^2$ | Physicochemical Data | Synthetic Method |
|---|---|---|---|---|
| 1 | —CH$_2$OH | 3-Cl-phenyl | mp 121.3–123.1° C. | 2 |
| 2 | —CH$_2$OCCH$_3$ (O) | 3-Cl-phenyl | mp 105.6–107.8° C. | 2 |
| 3 | —CH$_2$F | 3-Cl-phenyl | $n_D^{25}$ 1.5920 | 2 |
| 4 | —CBrF$_2$ | 3-Cl-phenyl | $n_D^{25}$ 1.5890 | 2 |
| 5 | —Br | 3-Cl-phenyl | $n_D^{25}$ 1.6317 | 2 |
| 6 | —CH$_2$—CH(O)CH$_2$ | 3-Cl-phenyl | $n_D^{25}$ 1.5965 | 2 |
| 7 | —CHF$_2$ | 3-Cl-phenyl | $n_D^{25}$ 1.4630 | 2 |
| 8 | —SO$_2$CH$_3$ | 3-Cl-phenyl | $n_D^{25}$ 1.4630 | 2 |

TABLE 1-continued
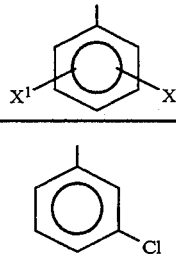
| Compound No. | R¹ | X¹ / X² | Physicochemical Data | Synthetic Method |
|---|---|---|---|---|
| 9 | —CH$_2$—CH=CH$_2$ | 3-Cl | $n_D^{25}$ 1.3148 | 2 |
| 10 | —CO$_2$C$_2$H$_5$ | 3-Cl | mp 83–86° C. | 2 |
| 11 | —CH$_2$—C≡CH | 3-Cl | mp 64.0–65.6° C. | 2 |
| 12 | —SO$_2$CF$_3$ | 3-Cl | mp 82.1–83.4° C. | 2 |
| 13 | —CH$_2$—CH=C(CH$_3$)$_2$ | 3-Cl | mp 78.8–79.8° C. | 2 |
| 14 | —CCl=CHCl | 3-Cl | mp 120–123° C. | 2 |
| 15 | —CH$_2$C(CH$_3$)=CH$_2$ | 3-Cl | $n_D^{25}$ 1.5930 | 2 |
| 16 | —CH$_2$CN | 3-Cl | $n_D^{25}$ 1.5970 | 2 |
| 17 | —CH$_2$CCl=CH$_2$ | 3-Cl | $n_D^{25}$ 1.5950 | 2 |

TABLE 1-continued

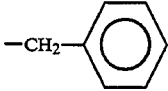

| Compound No. | R¹ | X¹ ⌬ X² | Physicochemical Data | Synthetic Method |
|---|---|---|---|---|
| 18 | -CH₂-⌬ | ⌬-Cl | mp 65.9–67.1° C. | 1 |
| 19 | -CH₂-⌬-Cl | ⌬-Cl | mp 106.4–107.4° C. | 2 |
| 20 | -CH₂-⌬-CH₃ | ⌬-Cl | mp 92.2–93.6° C. | 2 |
| 21 | -CH₂-⌬(Cl) | ⌬-Cl | $n_D^{25}$ 1.6092 | 2 |
| 22 | -CH₂-⌬-F | ⌬-Cl | mp 95.8–97.6° C. | 2 |
| 23 | -CH₂-⌬(N) | ⌬-Cl | mp 87.2–89.7° C. | 2 |
| 24 | -CH₂-⌬ | ⌬ | mp 72.5–73.9° C. | 1 |
| 25 | -CH₂-⌬(N) | ⌬ | $n_D^{25}$ 1.5950 | 2 |

EXAMPLE 3

Production of 2-(2-chloro-2-propenyl)-2-[2-(3-chlorophenyl)-2, 3-epoxypropyl]indane-1, 3-dione To a suspension of 0.56 g of 2-(2-chloro-2-propenyl)-2-[2-(3-chlorophenyl)propen-3-yl]indane-1, 3-dione and 0.17 g of sodium acetate trihydrate in 5 ml of chloroform was added 0.78 g of 40% peracetic acid, and the resultant mixture was refluxed for 4 hours under heating. Excess of the peroxide was inactivated with a 10% aqueous sodium thiosulfate solution, and the organic layer was washed with water, neutralized with aqueous saturated sodium bicarbonate, washed with water and aqueous saturated saline, dried over anhydrous magnesium sulfate, and the solvent was evaporated. The residue was chromatographed on a silica gel column, eluting with n-hexane/ethyl acetate (5:1) to give 0.35 g of Compound No. 34 listed in Table 2 below.

The compounds of Table 2 were prepared by the same methods as described above. The structures of the compounds were confirmed by IR and $^1$H-NMR data.

TABLE 2

[Structure: 2-substituted indane-1,3-dione with $R^1$ group and substituted phenyl with $X^1$ and $X^2$]

| Compound No. | $R^1$ | $X^1$, $X^2$ on phenyl | Physico-chemical Data |
|---|---|---|---|
| 26 | —Br | 3-Cl | $n_D^{25}$ 1.6088 |
| 27 | —CBrF$_2$ | 3-Cl | Viscous oil |
| 28 | —CH$_2$CH=CH$_2$ | 3-Cl | $n_D^{25}$ 1.5838 |
| 29 | —CH$_2$—CH(—O—)CH$_2$ (epoxide) | 3-Cl | $n_D^{25}$ 1.5880 |
| 30 | —CO$_2$C$_2$H$_5$ | 3-Cl | $n_D^{25}$ 1.5581 |
| 31 | —CH$_2$—C≡CH | 3-Cl | Viscous oil |
| 32 | —CH$_2$—C(CH$_3$)=CH$_2$ | 3-Cl | $n_D^{25}$ 1.5848 |
| 33 | —CH$_2$—C(CH$_3$)(—O—)CH$_2$ (epoxide) | 3-Cl | $n_D^{25}$ 1.5742 |
| 34 | —CH$_2$CCl=CH$_2$ | 3-Cl | $n_D^{25}$ 1.5930 |
| 35 | —CH$_2$CN | 3-Cl | mp 139.5–146.3° C. |
| 36 | —CH$_2$—C$_6$H$_5$ | 3-Cl | Viscous oil |
| 37 | —CH$_2$—(2-Cl-C$_6$H$_4$) | 3-Cl | Viscous oil |
| 38 | —CH$_2$—(4-F-C$_6$H$_4$) | 3-Cl | mp 93.9–97.2° C. |

EXAMPLE 4

Production of 2-benzyl-2-(2, 3-dihydroxy-2-phenylpropyl)indane-1, 3-dione.

To a solution of 1.0 g of 2-benzyl-2-(2-phenyl-2-propenyl)indane-1, 3-dione in 2 ml of 88% formic acid/2 ml of methylene chloride was added 0.44 ml of 35% hydrogen peroxide, and the resultant mixture was allowed to react at 60° C. for 3 hours. Excess peroxide was inactivated with a 10% aqueous sodium thiosulfate solution, and water was added to the reaction mixture, which was extracted with ethyl acetate. The organic layer was dried over anhydrous magnesium sulfate, and the solvent was evaporated. The residue was chromatographed on a silica gel column, eluting with n-hexane/ethyl acetate=1/1 to give 0.75 g of Compound No. 39 listed in the following Table 3.

The structure was confirmed by IR spectra and $^1$H-NMR spectra.

EXAMPLE 5

Production of 2-benzyl-2-(2-hydroxy-3-methylsulfonyloxy-2-phenylpropyl)indane-1, 3-dione To a solution of 0.69 g of 2-benzyl-2-(2, 3-dihydroxy-2-phenylpropyl)indane-1, 3-dione in 5 ml of pyridine was added 0.24 g of methanesulfonyl chloride, and the resultant mixture was stirred at room temperature for 12 hours. The reaction mixture was mixed with 3N hydrochloric acid and extracted with ethyl acetate. The organic layer was washed with water, dried over anhydrous magnesium sulfate and the solvent was evaporated. The residue was chromatographed on a silica gel column, eluting with n-hexane/ethyl acetate (1/1) to give 0.75 g of Compound No. 40 listed in Table 3.

The structure was confirmed by IR spectra and $^1$H-NMR spectra.

TABLE 3

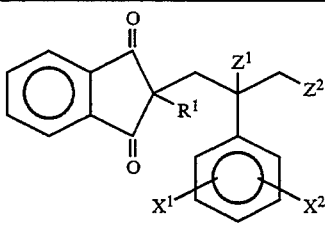

| Compound No. | $R^1$ | 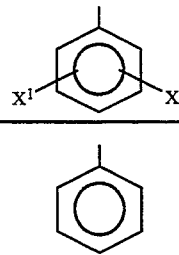 | $Z^1$ | $Z^2$ | Physicochemical Data |
|---|---|---|---|---|---|
| 39 | —CH$_2$—phenyl | phenyl | —OH | —OH | Amorphous Solid |
| 40 | —CH$_2$—phenyl | phenyl | —OH | —OSO$_2$CH$_3$ | mp 139.6–141.1° C. |

The following Table 4 shows IR and/or NMR spectra. (Compound Number of Table 4 corresponds to Compound No. of Table 1–3)

TABLE 4

| Compound No. | IR (cm$^{-1}$) or NMR δ [Solvent] |
|---|---|
| 1 | NMR [CDCl$_3$] 1.8(1H, br)3.05(2H, s)3.99(2H, s) 5.03(1H, s) 5.08(1H, s)6.60(1H, m)6.82(1H, m) 6.98–7.10(2H, m)7.62–7.78(4H, m) |
| 2 | IR KBr 1740, 1709, 1230, 1216 |
| 3 | NMR [CDCl$_3$] 2.92(2H, s)4.74(2H, d, J=0.16 ppm) 5.07(1H, s) 5.09(1H, s)6.60(1H, d)6.80(1H, dd) 7.06(2H, m) 7.70–7.80(4H, m) |
| 4 | IR Liquid Film 1750, 1713, 1591, 1248 |
| 5 | 1749, 1715, 1590, 1558, 1243 |
| 6 | 1743, 1706, 1593, 1352, 1244 |
| 7 | 1748, 1710, 1591, 1249 |
| 8 | 1743, 1706, 1891, 1317, 1248, 1137 |
| 9 | 398, 1742, 1705, 1593 |
| 10 | IR KBr 1750, 1725, 1703, 1590, 1240, 1220 3274, |
| 11 | 1741, 1701, 1593, 1560, 1352, 1244 |
| 12 | 1753, 1718, 1589, 1558, 1240 |
| 13 | NMR [CDCl$_3$] 1.442(3H, s)1.568(3H, s)2.57(2H, d) 3.052(2H, s) 4.75(1H, m)4.97(1H, s)5.02(1H, s) 6.38(1H, dd) 6.81(1H, dd) 7.02(1H, dd)7.03(1H, dd) 7.67(2H, m)7.70(2H, dd) |
| 14 | IR Liquid Film 1743, 1707, 1594, 1242 |
| 15 | NMR [CDCl$_3$] 1.41(3H, s)2.66(2H, s)3.06(2H, s) 4.46(2H, dd) 4.98(1H, d)5.03(1H, s)6.55(1H, d) 6.78(1H, dd) 7.01(1H, dd)7.09(1H, dd) 7.67(2H, dd) 7.71(2H, dd) |
| 16 | IR Liquid Film 2250, 1744, 1706, 1592, 1559, 1246 |
| 17 | 3440, 1744, 1707, 1629, 1592, 2558, 1245 |
| 18 | NMR [CDCl$_3$] 3.17(2H, s)3.19(2H, s)4.50(1H, s) 5.07(1H, s) 6.39(1H, dd)6.82(1H, dd) 6.9–7.1(7H, m) 7.52(2H, dd)7.56(2H, dd) |
| 19 | 3.14(2H, s)3.16(2H, s)5.00(1H, s) 5.07(1H, s) 6.56(1H, d)6.79(1H, dd)6.89(1H, dd) 7.93–7.10(5H, m)7.53(2H, dd) 7.60(2H, dd) |
| 20 | 1.20(3H, s)3.06(4H, s) 4.99(1H, s)5.06(1H, s) 6.57(1H, d)6.75–6.88(5H, m) 6.97–7.10(2H, m) 7.52(2H, dd)7.58(2H, dd) |
| 21 | IR KBr 3406, 2974, 2936, 1705, 1602, 1222 |
| 22 | NMR [CDCl$_3$] 3.16(4H, d)5.00(1H, d)5.06(1H, s) 6.56(1H, d) |

TABLE 4-continued

| Compound No. | IR (cm$^{-1}$) or NMR δ [Solvent] |
|---|---|
| | 6.67(2H, dd)6.80(1H, dd) |
| | 6.92(2H, dd) |
| | 7.01(1H, dd)7.09(1H, dd) |
| | 7.51(2H, dd) |
| | 7.59(2H, dd) |
| 23 | 3.17(2H, s)3.18(2H, s)5.01(1H, s) |
| | 5.08(1H, s) |
| | 6.52(1H, t)6.79(1H, dd) |
| | 6.93(1H, dd)7.02(1H, t) |
| | 7.09(1H, dd)7.30(1H, m)7.5(2H, m) |
| | 7.6(2H, m) |
| | 8.24(2H, dd) |
| 24 | IR        KBr |
| | 1736, 1701, 1589, 1354, 1244 |
| 25 | IR        Liquid Film |
| | 1744, 1707, 1591, 1434, 1246 |
| 26 | 3456, 1750, 1716, 1597, 1271, 1244 |
| 27 | NMR        [CDCl$_3$] |
| | 2.52(1H, d)2.90(1H, d)2.95(1H, d) |
| | 3.21(1H, d) |
| | 6.79(1H, d)7.01(1H, dd)7.15(2H, m) |
| | 7.82(2H, dd)7.96(2H, dd) |
| 28 | IR |
| | 3348, 1743, 1706, 1596 |
| 29 | IR        Liquid Film |
| | 3060, 2996, 2920, 1743, 1705, 1595, 1241 |
| 30 | 3425, 1759, 1709, 1596, 1252, 1210 |
| 31 | 3230, 1744, 1707, 1595, 1423, 1352, 1243 |
| 32 | 3434, 1741, 1703, 1593, 1561, 1473, |
| | 1428, 1357, 1243 |
| 33 | NMR        [CDCl$_3$] |
| | 1.05(3H, s)2.02(1H, d)2.05(1H, s) |
| | 2.26(1H, d) |
| | 2.35(1H, d)2.41(3H, m)2.41(2H, m) |
| | 2.72(1H, d)2.80(1H, d)6.61(1H, dd) |
| | 6.91(1H, dd)7.07(1H, dd) |
| | 7.10(1H, dd) |
| | 7.60(1H, dd)7.72(1H, dd) |
| 34 | IR        Liquid Film |
| | 3170, 2910, 1743, 1705, 1630, 1596, 1242 |
| 35 | IR        KBr |
| | 2964, 2250, 1744, 1708, 1592, 1426, 1245 |
| 36 | IR        Liquid Film |
| | 3430, 1740, 1703, 1596, 1245 |
| 37 | 3006, 2924, 1741, 1706, 1595, 1570, |
| | 1474, 1427, 1369, 1245 |
| 38 | IR        KBr |
| | 2922, 1743, 1703, 1594, 1503, 1245, 1221 |
| 39 | KBr |
| | 3400, 1720, 1705, 1600, 1490, 1455 |
| 40 | Liquid Film |
| | 3400, 1720, 1710, 1602, 1447, 1333, 1239, 1171 |

Formulation Examples of the compounds of the present invention will be shown below. The "part" and "%" in the following Examples mean "parts by weight" and "% by weight", respectively.

FORMULATION EXAMPLE 1

Wettable Powder

A uniform mixture of 40 parts of the compound of the present invention in Tables 1-3, 20 parts of Carplex No. 80 (Shionogi & Co., Ltd., Trademark), 35 parts of N, N Kaolin Clay (Tsuchiya Kaolin Co., Trademark) and 5 parts of Sorpol 8070 (Toho Kagaku Company, Trademark), a higher alcohol sulfate surfactant, was pulverized to give wettable powder containing 40% of the active ingredient.

FORMULATION EXAMPLE 2

Granule

A uniform mixture of 1 part of the compound of the present invention in Tables 1-3, 45 parts of clay (Nippon Talc Company), 52 parts of bentonite (Houjun Yoko Company) and 2 parts of Airoll CT-1 (Toho Kagaku Company, Trademark), a succinate surfactant, was pulverized, mixed with 20 parts of water and kneaded. The resultant mixture was extruded from an extruding granulator with holes having 0.6 mm diameter, and the resultant nudles were cut 1-2 mm long to give granules containing 1% of the active ingredient.

FORMULATION EXAMPLE 3

Emulsion

To a solution of 30 parts of the compound of the present invention in Tables 1-3 dissolved in a mixed solvent of 30 parts of xylene and 25 parts of dimethylformamide was added 15 parts of Sorpol 3005 X (Toho Kagaku Company, Trademark), a polyoxyethylene surfactant to give an emulsion containing 30% of the active ingredient.

FORMULATION EXAMPLE 4

Flowable

Into a mixture of 8 parts of ethylene glycol, 5 parts of Sorpol AC3032 (Toho Kagaku Company, Trademark), 0.1 part of xanthan gum and 56.9 parts of water was throughly dispersed 30 parts of the compound of the present invention in Tables 1-3. The resultant slurry mixture was pulverized wet with Dyno mill (Shinmaru Enterprises Company) to give a stable flowable containing 30% of the active ingredient.

EXPERIMENT 1

Paddy Soil Treatment Test

A resin pot of 200 cm$^2$ area was filled with paddy field offing-accumulated soil, which was then fertilized and mixed with an appropriate amount of water. After scratching the soil, seeds of barnyardgrass, pickerelweed, and hardstem bulrush were incorporated into the soil at the surface layer of 0.5 cm thick. Rice plant seeding (strain: Akinishiki) at 2.1 leaf age was then transplanted by one stump (3 stalks per stump), and water was poured to the pot and about 3.5 cm of depth of water was kept.

Five days after sowing the weed seeds and transplanting the rice plant seeding, the wettable powder obtained in Formulation Example 1 was dropwise added to the pot surface so that 10, 5, 2.5 and 1.25 g per 1 are of the active ingredient were applied. As active controls, two wettable powders containing (A) 2-[2-(3-chlorophenyl)-2,3-epoxypropyl]-2-ethylindane-1,3-dione (Control A) and (B) S-4-chlorobenzyl diethyl thiocarbamate (Control B) respectively were prepared and applied to the pot surface in the same manner as above. Control A is disclosed in Japanese Patent Publication (Kokai) No. 304043/1990 and Control B is commercially available.

Cultivation was conducted in the greenhouse, and 21st day after treatment with the above chemicals, herbicidal effects and damage on the rice plant were examined.

Table 5 shows the experimental results, in which Compound numbers are those listed in Tables 1-3. Evaluation of herbicidal effects was conducted based on the following equation and criteria.

$$\left(1 - \frac{\text{Live Body (above ground) Weight of Weed in Treated Section}}{\text{Live Body (above ground) Weight of Weed in Non-treated Section}}\right) \times 100 = Y(\%)$$

| CRITERIA | |
|---|---|
| Herbicidal Coefficient | Y (%) |
| 0 | 0–5 |
| 1 | 6–30 |
| 2 | 31–50 |
| 3 | 51–70 |
| 4 | 71–90 |
| 5 | 90–100 |

Evaluation of magnitude of damage on rice plant was effected based on the following equation and criteria:

$$\left(1 - \frac{\text{Live Body (above ground) Weight of Crop in Treated Section}}{\text{Live Body (above ground) Weight of Crop in Non-treated Section}}\right) \times 100 = Y(\%)$$

| CRITERIA | |
|---|---|
| Damage Coefficient | Y (%) |
| 0 | 0–5 |
| 1 | 6–10 |
| 2 | 11–20 |
| 3 | 21–40 |
| 4 | 41–60 |
| 5 | 61–100 |

TABLE 5

| Compound No. | Application Rate g/a | Herbicidal Coefficient | | | Damage Coefficient |
|---|---|---|---|---|---|
| | | barnyard-grass | pickerel-weed | hardstem bulrush | Transplanted Rice Plant |
| 1 | 2.5 | 5 | 5 | 5 | 0 |
| | 1.25 | 4 | 5 | 3 | 0 |
| 3 | 2.5 | 5 | 5 | 5 | 0 |
| | 1.25 | 5 | 5 | 4 | 0 |
| 4 | 2.5 | 5 | 5 | 5 | 0 |
| | 1.25 | 5 | 5 | 4 | 0 |
| 7 | 2.5 | 5 | 5 | 5 | 1 |
| | 1.25 | 5 | 5 | 4 | 0 |
| 9 | 2.5 | 5 | 5 | 4 | 0 |
| | 1.25 | 4 | 4 | 3 | 0 |
| 11 | 2.5 | 5 | 5 | 5 | 0 |
| | 1.25 | 5 | 5 | 4 | 0 |
| 13 | 2.5 | 5 | 5 | 5 | 0 |
| | 1.25 | 5 | 4 | 3 | 0 |
| 14 | 2.5 | 5 | 5 | 5 | 1 |
| | 1.25 | 5 | 5 | 4 | 0 |
| 15 | 2.5 | 5 | 5 | 5 | 0 |
| | 1.25 | 4 | 4 | 3 | 0 |
| 16 | 2.5 | 5 | 5 | 4 | 0 |
| | 1.25 | 4 | 4 | 3 | 0 |
| 17 | 2.5 | 5 | 5 | 5 | 0 |
| | 1.25 | 5 | 5 | 4 | 0 |
| 18 | 2.5 | 5 | 5 | 5 | 0 |
| | 1.25 | 5 | 5 | 4 | 0 |
| 20 | 2.5 | 5 | 5 | 4 | 0 |
| | 1.25 | 3 | 5 | 3 | 0 |
| 21 | 2.5 | 5 | 5 | 4 | 0 |
| | 1.25 | 5 | 4 | 3 | 0 |
| 22 | 2.5 | 5 | 5 | 4 | 0 |
| | 1.25 | 5 | 4 | 4 | 0 |
| 23 | 2.5 | 5 | 5 | 5 | 0 |
| | 1.25 | 5 | 4 | 3 | 0 |
| 27 | 2.5 | 5 | 5 | 5 | 0 |
| 28 | 1.25 | 5 | 5 | 5 | 0 |
| | 2.5 | 5 | 5 | 5 | 1 |
| 29 | 1.25 | 5 | 5 | 4 | 0 |
| | 2.5 | 5 | 5 | 5 | 1 |
| 30 | 1.25 | 5 | 5 | 5 | 0 |
| | 2.5 | 5 | 5 | 5 | 0 |
| 31 | 1.25 | 5 | 5 | 4 | 0 |
| | 2.5 | 5 | 5 | 5 | 2 |
| 33 | 1.25 | 5 | 5 | 4 | 0 |
| | 2.5 | 5 | 5 | 5 | 1 |
| 34 | 1.25 | 5 | 5 | 5 | 0 |
| | 2.5 | 5 | 5 | 5 | 1 |
| 35 | 1.25 | 5 | 5 | 5 | 0 |
| | 2.5 | 5 | 5 | 5 | 1 |
| 36 | 1.25 | 5 | 5 | 5 | 0 |
| | 2.5 | 5 | 5 | 4 | 0 |
| 37 | 1.25 | 5 | 5 | 5 | 0 |
| | 2.5 | 5 | 5 | 5 | 0 |
| 37 | 1.25 | 5 | 5 | 5 | 0 |
| | 2.5 | 5 | 5 | 5 | 0 |
| 38 | 1.25 | 5 | 5 | 5 | 0 |
| | 2.5 | 5 | 5 | 5 | 0 |
| 40 | 1.25 | 5 | 5 | 5 | 0 |
| | 2.5 | 5 | 5 | 5 | 0 |
| Compound (A) | 5 | 5 | 5 | 5 | 2 |
| | 2.5 | 5 | 4 | 4 | 0 |
| Compound (B) | 10 | 4 | 3 | 4 | 0 |
| | 5 | 3 | 1 | 2 | 0 |
| Non-treated Section | — | 0 | 0 | 0 | 0 |

EXPERIMENT 2

Field Soil Treatment

A resin vat having 400 cm² area was filled with volcanic ashes soil, and crop seeds (corn and soybean) were sown on the soil surface. The seeds were covered with 2 cm thick of soil. The soil surface was uniformly mixed with other soil containing weed seeds (large crabgrass and green foxtail) and treated with the wettable powder obtained in Formulation Example 1 and two wettable powders containing Control Compounds (A) and (B) as described in Experiment 1. These powders were applied on the surface of the soil by a small-sized compressing sprinkler so that 20, 10 and 5 g per 1 are of the active ingredients were applied.

Cultivation was conducted in the greenhouse, and 21st day after treatment with the chemicals the herbicidal effect and damage on the crops were examined.

Table 6 shows the experimental results, in which Compound numbers are those listed in Tables 1–3. Evaluation of herbicidal effects and damage on the crops were represented on the same standard as in Experiment 1.

TABLE 6

| Compound No. | Application Rate g/a | Herbicidal Coefficient | | Damage Coefficient | |
|---|---|---|---|---|---|
| | | large crabgrass | green foxtail | Corn | Soybean |
| 4 | 5 | 5 | 5 | 0 | 0 |
| 7 | 5 | 5 | 5 | 0 | 0 |
| 9 | 5 | 5 | 5 | 0 | 0 |
| 10 | 5 | 5 | 5 | 0 | 0 |
| 11 | 5 | 5 | 5 | 0 | 0 |
| 13 | 5 | 5 | 4 | 0 | 0 |
| 15 | 5 | 5 | 5 | 0 | 0 |

TABLE 6-continued

| Compound No. | Application Rate g/a | Herbicidal Coefficient large crabgrass | Herbicidal Coefficient green foxtail | Damage Coefficient Corn | Damage Coefficient Soybean |
|---|---|---|---|---|---|
| 16 | 5 | 5 | 5 | 0 | 0 |
| 17 | 5 | 5 | 4 | 0 | 0 |
| 18 | 5 | 5 | 5 | 0 | 0 |
| 22 | 5 | 5 | 5 | 0 | 0 |
| 27 | 5 | 5 | 4 | 0 | 0 |
| 28 | 5 | 5 | 4 | 0 | 0 |
| 29 | 5 | 5 | 4 | 0 | 0 |
| 31 | 5 | 5 | 5 | 0 | 0 |
| 33 | 5 | 5 | 5 | 0 | 0 |
| 34 | 5 | 5 | 4 | 0 | 0 |
| 35 | 5 | 5 | 5 | 0 | 0 |
| 36 | 5 | 5 | 4 | 0 | 0 |
| 37 | 5 | 5 | 4 | 0 | 0 |
| 38 | 5 | 5 | 5 | 0 | 0 |
| 40 | 5 | 4 | 4 | 0 | 0 |
| Compound (A) | 10 | 5 | 5 | 1 | 0 |
| Compound (B) | 20 | 4 | 3 | 0 | 0 |
| Non-treated section | — | 0 | 0 | 0 | 0 |

The compounds of the present invention are highly valuable and have excellent herbicidal activity with markedly low damage on crops.

What is claimed is:

1. A compound of the formula

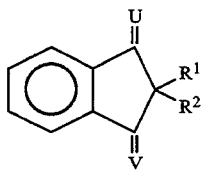

wherein $R^1$ represents $C_2$-$C_{10}$ alkenyl, $C_2$-$C_6$ alkynyl, $C_1$-$C_6$ haloalkyl, $C_2$-$C_6$ haloalkenyl, $C_1$-$C_4$ hydroxylalkyl, $C_2$-$C_5$ alkoxy carbonyl, halogen, $C_2$-$C_4$ cyanoalkyl, or —$CH_2$-A, in which A represents phenyl, pyridyl, or oxiranyl, said phenyl and pyridyl groups being unsubstituted or substituted by halogen, $C_1$-$C_3$ alkyl, hydroxy, $C_1$-$C_4$ alkoxy, $C_1$-$C_4$ alkylthio, nitro or cyano;

$R^2$ represents

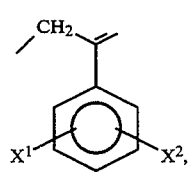

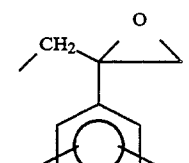

or

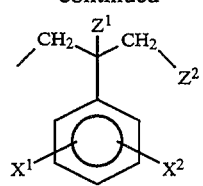

in which $X^1$ and $X^2$ each independently represent hydrogen, halogen, $C_1$-$C_4$ alkyl, $C_1$-$C_3$ haloalkyl or nitro; $Z^1$ and $Z^2$ each independently represent hydroxy, or $C_1$-$C_4$ alkylsulfonyloxy; and U and V represent oxygen.

2. A compound according to claim 1, wherein $R^1$ represents $C_2$-$C_{10}$ alkenyl, $C_2$-$C_6$ alkynyl, $C_1$-$C_6$ haloalkyl, $C_2$-$C_6$ haloalkenyl, $C_1$-$C_4$ hydroxyalkyl, halogen, $C_2$-$C_4$ cyanoalkyl, or —$CH_2$-A, in which A is as defined in claim 1;

$R^2$ represents

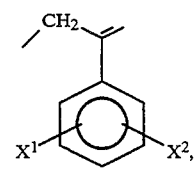

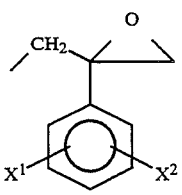

or

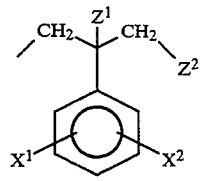

in which $X^1$ and $X^2$ each independently represent hydrogen or halogen; $Z^1$ and $Z^2$ each independently represent hydroxy, or $C_1$-$C_4$ alkylsulfonyloxy; and U and V represent oxygen.

3. A compound according to claim 1 wherein $R^1$ represents $C_2$-$C_{10}$ alkenyl, $C_2$-$C_6$ alkynyl, $C_1$-$C_6$ haloalkyl, $C_1$-$C_4$ hydroxyalkyl, $C_2$-$C_5$ alkoxy carbonyl, halogen, $C_2$-$C_4$ cyanoalkyl, or —$CH_2$-A, in which A represents optionally substituted phenyl or pyridyl as defined in claim 1;

$R^2$ represents

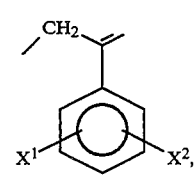

-continued

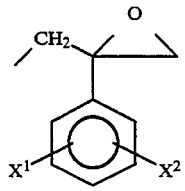

or

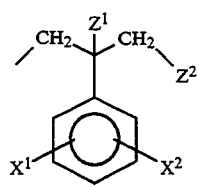

in which one of $X^1$ and $X^2$ represents hydrogen or halogen, and the other represents hydrogen; $Z^1$ and $Z^2$ each independently represent hydroxy or $C_1$-$C_4$ alkylsulfonyloxy; and U and V represent oxygen.

4. A compound according to claim 3, wherein $R^1$ is $C_2$-$C_{10}$ alkenyl, $C_2$-$C_6$ alkynyl, $C_1$-$C_6$ haloalkyl, $C_2$-$C_6$ haloalkenyl, $C_2$-$C_5$ alkoxycarbonyl, halogen, $C_2$-$C_4$ cyanoalkyl, or —$CH_2$-A, in which A represents optionally substituted phenyl or pyridyl as defined in claim 3.

5. A compound according to claim 3 wherein $R^2$ is

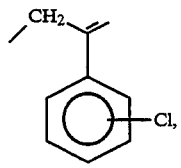

-continued

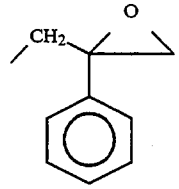

or

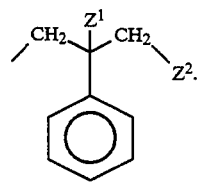

6. A compound according to claim 3, wherein $R^1$ is $C_2$-$C_6$ alkenyl, $C_2$-$C_4$ alkynyl, $C_1$-$C_6$ haloalkyl containing one to three halogen atoms, $C_2$-$C_4$ haloalkenyl containing one to three halogen atoms, $C_2$-$C_4$ alkoxycarbonyl, bromine, cyanomethyl, or —$CH_2$-A, in which A represents phenyl or pyridyl which groups are unsubstituted or are substituted with $C_1$-$C_3$ alkyl or halogen.

7. A herbicidal composition which comprises as an essential component a herbicidally effective amount of a compound as defined in claim 1 together with a suitable carrier therefor.

8. A herbicidal composition which comprises as an essential component a herbicidally effective amount of a compound as defined in claim 3 together with a suitable carrier therefor.

9. A herbicidal composition which comprises as an essential component a herbicidally effective amount of a compound as defined in claim 4 together with a suitable carrier therefor.

10. A herbicidal composition which comprises as an essential component a herbicidally effective amount of a compound as defined in claim 5 together with a suitable carrier therefor.

11. A herbicidal composition which comprises as an essential component a herbicidally effective amount of a compound as defined in claim 6 together with a suitable carrier therefor.

* * * * *